US009461992B2

(12) United States Patent
Outwater et al.

(10) Patent No.: US 9,461,992 B2
(45) Date of Patent: Oct. 4, 2016

(54) SMARTPHONE BASED IDENTIFICATION, ACCESS CONTROL, TESTING, AND EVALUATION

(71) Applicants: Chris Outwater, Santa Barbara, CA (US); William Gibbens Redmann, Glendale, CA (US)

(72) Inventors: Chris Outwater, Santa Barbara, CA (US); William Gibbens Redmann, Glendale, CA (US)

(*) Notice: Subject to any disclaimer, the term of this patent is extended or adjusted under 35 U.S.C. 154(b) by 162 days.

(21) Appl. No.: 14/149,158

(22) Filed: Jan. 7, 2014

(65) Prior Publication Data
US 2014/0223531 A1    Aug. 7, 2014

Related U.S. Application Data

(60) Provisional application No. 61/750,390, filed on Jan. 9, 2013.

(51) Int. Cl.
G06F 7/04        (2006.01)
H04L 29/06       (2006.01)
G06K 9/00        (2006.01)

(52) U.S. Cl.
CPC ....... H04L 63/0861 (2013.01); G06K 9/00845 (2013.01); G06K 9/00885 (2013.01); H04L 63/083 (2013.01); H04L 63/0853 (2013.01)

(58) Field of Classification Search
None
See application file for complete search history.

(56) References Cited

U.S. PATENT DOCUMENTS

| | | | | |
|---|---|---|---|---|
| 4,857,916 A * | 8/1989 | Bellin | ............... | G06K 9/00375 340/5.52 |
| 5,229,764 A * | 7/1993 | Matchett | ............ | G07C 9/00158 340/5.52 |
| 8,051,468 B2 * | 11/2011 | Davis | ..................... | G06F 21/32 713/186 |
| 8,549,318 B2 | 10/2013 | White | | |
| 2004/0002894 A1 * | 1/2004 | Kocher | .............. | G07C 9/00087 705/13 |
| 2004/0059923 A1 * | 3/2004 | ShamRao | ............... | G06F 21/32 713/186 |
| 2006/0136741 A1 * | 6/2006 | Mercredi | ................ | G06F 21/32 713/185 |
| 2006/0280340 A1 * | 12/2006 | Derakhshani | ...... | G06K 9/00597 382/117 |
| 2007/0248242 A1 * | 10/2007 | Ritter | ................. | G07C 9/00158 382/100 |
| 2008/0104415 A1 * | 5/2008 | Palti-Wasserman | .... | G06F 21/32 713/186 |
| 2008/0148393 A1 * | 6/2008 | Wendt | ..................... | G06F 21/32 726/19 |
| 2008/0166028 A1 * | 7/2008 | Turek | ................... | G06K 9/0002 382/124 |
| 2009/0024050 A1 * | 1/2009 | Jung | ....................... | A61B 5/16 600/544 |
| 2009/0083850 A1 * | 3/2009 | Fadell | ................... | G06F 21/316 726/19 |
| 2010/0246902 A1 * | 9/2010 | Rowe | ................. | G06K 9/00033 382/115 |
| 2011/0157347 A1 | 6/2011 | Kalocsai | | |
| 2011/0197270 A1 * | 8/2011 | Kaufman | ................. | G06F 21/32 726/7 |
| 2012/0022958 A1 * | 1/2012 | de Sylva | .............. | G06Q 20/209 705/24 |
| 2012/0078473 A1 * | 3/2012 | Ridder | ................. | A61B 5/0071 701/45 |
| 2012/0083668 A1 | 4/2012 | Pradeep | | |
| 2012/0164978 A1 * | 6/2012 | Conti | ..................... | G06F 21/32 455/411 |

OTHER PUBLICATIONS

PCT International search report and opinion for PCT/US15/10409, Apr. 13, 2015 (PCT from instant application).

* cited by examiner

Primary Examiner — Kenny Lin
(74) Attorney, Agent, or Firm — Clifford H. Kraft

(57) ABSTRACT

A suite of testing and evaluation tools that run in conjunction with a smartphone that can be used to both enroll, and for subsequent enrollees, to gain secure access so that the program may measure, track and report on tests, including activities, that may indicate general health and wellness status. Here, the word "smartphone" includes any handheld or mobile device containing at least one processor. The smartphone can be used as the platform for this suite of tools that can include applications that run independently on the smartphone device, but can also include sensors and other data acquisition tools that can be peripheral to the smartphone and connected by wire or wirelessly.

20 Claims, 5 Drawing Sheets

SMARTPHONE BASED IDENTIFICATION, ACCESS CONTROL, TESTING, AND EVALUATION

This application is related to, and claims priority from, U.S. Provisional Patent application No. 61/750,390 filed Jan. 9, 2013. Application 61/750,390 is hereby incorporated by reference in its entirety.

BACKGROUND

1. Field of the Invention

The present invention relates to the field of identification, access control and evaluation and more particularly relates to using a smartphone in this application.

2. Description of the Prior Art

The modern mobile communication device, such as the cellular telephone or so-called smart cellular telephone (smartphone) has become almost ubiquitous in society. Most adults and teenagers routinely carry these devices as well as a number of younger children. The smartphone incorporates considerable processing power and sophisticated communications with a powerful display system and embedded sensors.

The smartphone also promises to become the portal allowing secure personal authentication, mental and physical evaluation and secure access control. The smartphone will become the preferred tool for the "accountable care process", and everything that this proposed health insurance system contemplates will demand both secure identification and ubiquitous ease of use for quickly and repeatedly determining levels of health and competence over a wide range of activities, as well as subsequent calculation of the risks within a group of insured individuals.

Risk management will become the primary focus of health providers as they navigate the new health insurance frontiers. They must inform and motivate their partners and customers so that they can mitigate their risks. Patients will strive to be healthier because they will be rewarded for their efforts. Health teams will be organized and promoted. Effective, inexpensive tools for monitoring health will be in great demand.

Biometric ID hardware and software will be readily available on many smartphones. Fingerprint, facial recognition, voice recognition will all be used to secure the ID and to access information. This will be especially true for individuals who are seeking help in maintaining their health at specific levels. Employers will be instilling a "team spirit" as all employees strive to maintain the costs of health care for their group.

SUMMARY OF THE INVENTION

The present invention presents a suite of testing and evaluation tools that run in conjunction with a smartphone that can be used to both enroll individuals and subsequently allow such enrollees to gain secure access so that the program may measure, track and report on tests, including activities, that may indicate general health and wellness status. Here, the word "smartphone" includes any handheld or mobile device containing at least one processor. The smartphone can be used as the platform for this suite of tools that can include applications that run independently on the smartphone device or in communication with it, but can also include sensors and other data acquisition tools that can be peripheral to the smartphone and connected by wire or wirelessly.

As a first step in the process, the present invention utilizes biometric and PIN techniques to enroll and identify patients. Next, the smartphone can be used to both identify enrollees and to directly monitor external conditions. The present invention comprises a suite of access, testing and evaluation tools, whether running local applications (apps), communicating with remote, cloud based servers, or a combination of these to attain a secure and efficient testing platform that can be used by enrollees to measure, track and report on tests, including activities that may indicate health and wellness status. The smartphone is used as the platform for this suite of tools that can include applications that run independently on the smartphone device, but can also include sensors and other data acquisition tools that can be peripheral to the smartphone and connected by wire or wirelessly. Such basic health parameters as temperature, pulse, blood oxygen, blood pressure, weight, and the like can also be captured by the mobile device. The present invention uses the existing data capture and display and kinetic measurement devices inherent to the modern mobile communication devices, such as smartphones, to utilize the enrollee's visual, auditory and tactile senses in order to determine general physical and mental health status and alertness. These may all be used in order to calculate a general wellness status and derive a risk profile. In another embodiment the present invention can determine and control access to vehicular assets.

DESCRIPTION OF THE FIGURES

Attention is now directed to several drawings that illustrate features of the present invention.

Several drawings and illustrations have been presented that aid in understanding the present invention. The scope of the present invention is not limited to what is shown in the figures.

DESCRIPTION OF THE PREFERRED EMBODIMENTS

Figure 1:
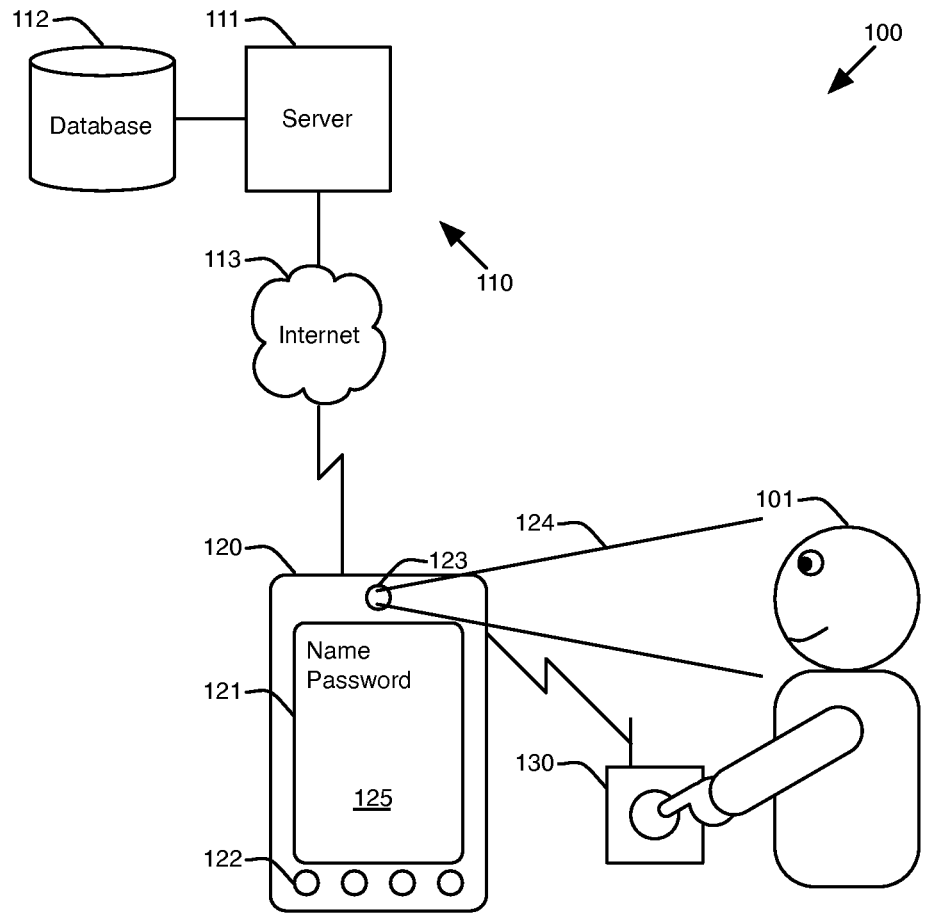
FIG. 1 shows a smartphone-based secure health testing and access system being used in one example of a self-enrollment process.

FIG. 1 shows one of the first steps in the process of the present invention: enrollment. Enrollment 125 (on screen 121) depends on the proper identity of the enrollee 101; therefore, various levels of identity assurance can be used to authenticate and confirm an enrollee's identity. As mentioned, many smartphones 120 are progressing to biometric based access to the wireless phone's basic operations. During online or in-person enrollment, the enrollee 101 can create a secure account by taking a smartphone photo 124 with camera 123 of a certified picture ID (not shown) such as a passport, drivers license, or both. It is well known in the art that hardware and software already exists for photographically scanning checks and credit cards. Similar software can be used to scan certified photos to complement existing personal identity verification tools. This graphical information can be tied to the smartphone telephone number and can be checked against the identity of the registered owner of the telephone. This information can also be tied to any other biometrics that are required for access to the phone's operation. The required number and nature of biometrics, whether facial recognition (using photo 124 of enrollee), voiceprint, spoken passphrase (microphone not shown), fingerprint 130, etc., depends on the policy of the administrative entity and the level of security required.

FIG. 1 shows a self-enrollment process with the system of the present invention. For any heightened access level a (live) photo 124 of the enrollee can be submitted and a voice pattern (not shown) or fingerprint, using sensor 130, can be given. This might be required for doctors and nurses to write to and modify an existing enrollee record based on HIPPA regulations. Any latency in voice and/or image data recording and transmission can be accounted for, and the data can be correlated and processed on high speed servers 111 in a cloud server environment (i.e., through Internet 113) or elsewhere. All data can be tied to the enrollee's personal account 112. The enrollee can allow various levels of access to the personal account based on HIPPA rules, policy, as may health coaches, insurance companies, nurses, law enforcement, and the like.

Figure 2:
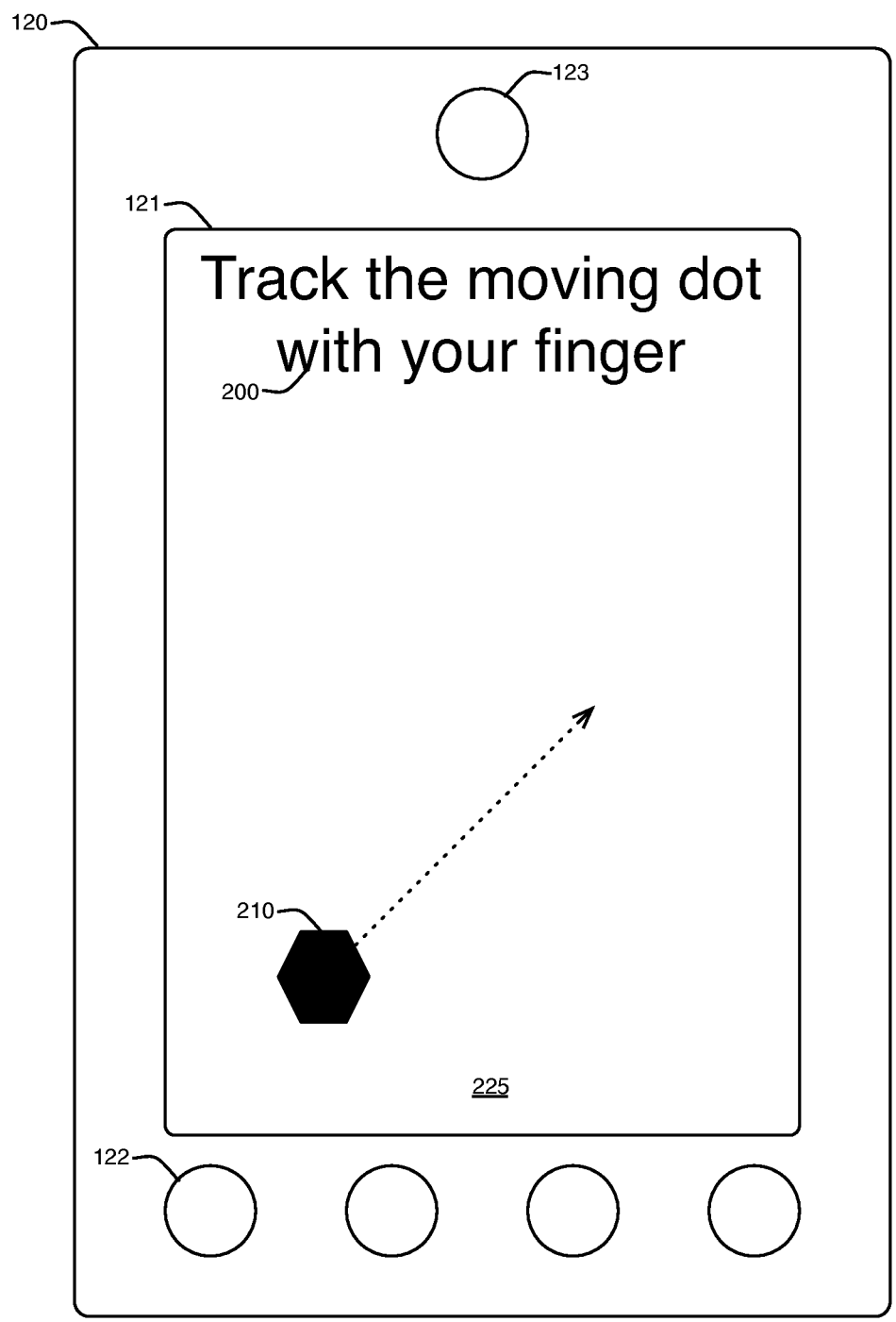
FIG. 2 shows the use of a smartphone-based secure health testing and access system in use for one example kinetic assessment.

FIG. 2 shows, in a particular embodiment of the present invention, kinetic testing in conjunction with voice or visual instructions 200. Instructions to move, transfer from one hand to another, screen 121 face up, screen 121 face down, graphical arrow on screen up, arrow on screen down. Actions such as keeping an arrow always facing up by rotating the phone as the arrow rotates on screen is also possible. Other instructions based on color are also possible, such as, if arrow turns from red to blue, point the arrow down. This type of testing is a valuable tool in accessing the general neurological condition of the subject. It can thus be used for general assessment by first responders and, outside the medical realm by police. Another example test, shown in FIG. 2, direct the subject to track the moving dot 210 on screen 121 with their finger (if screen 121 is a touchscreen), or with controls, e.g. 122, otherwise.

This process can also be used as an assessment and access tool for vehicles of all types. The smartphone can be wirelessly tuned or otherwise connected to an on-board diagnostic (OBD) connector and could be tied to mandatory access testing for at risk individuals with some record of criminal activity such as a parolee or a person previously convicted of driving under the influence of alcohol or drugs. Access can range from small motor vehicles to major vehicular assets such as planes, ships, trains, and the like. Owners and enforcement officials can choose from a suite of smartphone-based tests based on enrollee's profile and a range of security and risk management demands.

Figure 3A:
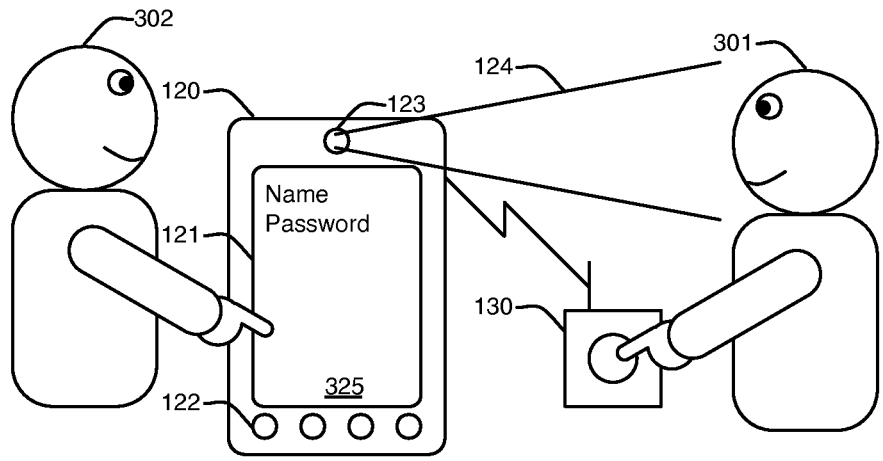
FIG. 3A shows a smartphone-based secure health testing and access system being used in one example secure enrollment process monitored by an authorized third person.
Figure 3B:
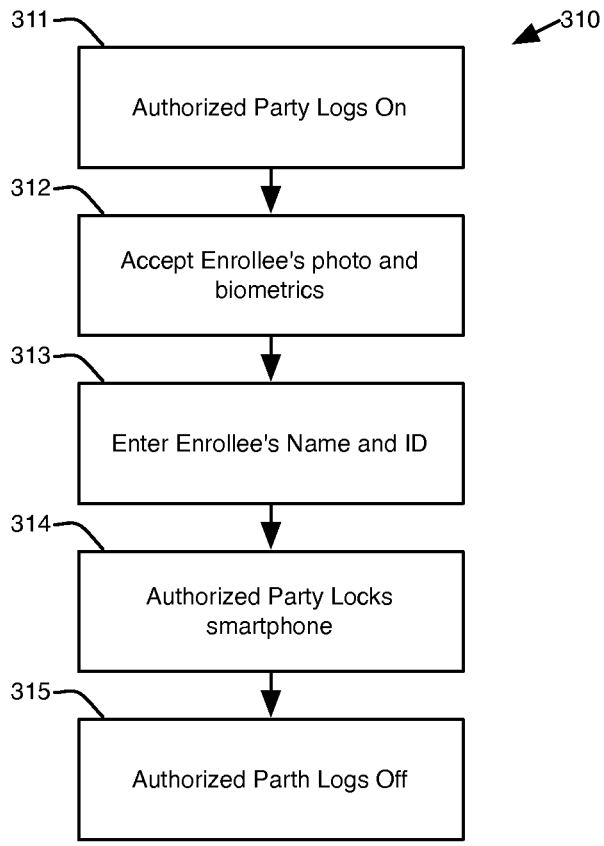
FIG. 3B is a flowchart for that monitored enrollment process.

FIG. 3A illustrates and enrollment procedure 325 for use in some higher security applications, there may be need for a person of authority 302 to register the owner 301 of the smartphone using a secure password or other means of identification. The smartphone is the key or portal to virtual or real world access to people, places and objects of value, such as, machines, vehicles, devices, locations, and other access. In some cases the enrollee 301 is enrolled not by himself (as enrollee 101 was in FIG. 1), but by a person of authority 302 who locks-in the enrollee's ID into the smartphone and a chosen list of functions by virtue of a secure password or biometric such that the attachment of the smartphone to that enrollee cannot be changed without knowledge of the password and the biometrics of the enroller 302. This secure administrative process can take place in person or in an online registration session. FIG. 3B shows the secure registration process 310 for a third person beginning at step 311 where the authorized party 302 logs on. At step 312, the enrollee's 301 photo 124 and biometrics (e.g., fingerprint via reader 130) are accepted. At step 313, the enrollee's name and ID are entered, e.g. via form 325 on screen 121 or photo of ID as described above. At step 314 the authorized party 302, having at least monitored the performance of steps 312, 313, locks-in the enrollee's ID into the smartphone, and subsequently (in step 315) logs off.

The present invention provides a suite of access, testing and evaluation tools whether running local applications (apps) on smartphone 120, or apps communicating with remote, cloud-based 113 servers 111 (or local servers), or a combination of these to attain a secure and efficient testing platform that can be used by enrollees 101, 401 to measure, track and report on tests, including activities (e.g., as shown in FIG. 2) that may indicate the health and wellness status. The smartphone 120 can be used as the platform for this suite of tools that can include applications that run independently on the smartphone device, but can also include sensors and other data acquisition tools (e.g., fingerprint sensor 130) that can be peripheral to the smartphone and connected by wire or wirelessly. Such basic health parameters as temperature, pulse, blood oxygen, blood pressure, weight, and the like can thus be captured by the mobile device. The present invention can use the existing data capture, display and kinetic measurement devices inherent to the modern mobile communication devices, such as smartphones, to utilize the enrollee's visual, auditory and tactile senses in order to determine general physical and mental health status and alertness which may all be used in order to calculate a general wellness status and derive a risk profile, not only a health risk profile, but in another embodiment discussed below in conjunction with FIGS. 4A and 4B, to determine and control access to vehicular assets. Ease of use and frequency of use is vital, thus the ubiquitous mobile device, with all of its built-in data capture and display devices, or a similar device is important to the invention.

In a particular embodiment, the camera, microphone and LCD screen, accelerometers and vibration device can be used to test the alertness of the enrollee. This can be done by testing various senses: visual, auditory, tactile in conjunction with measuring the reaction time to each requested operation by the enrollee. This process and the instructions should be language neutral, that is, either in the language of the enrollee's preference, or in a pictographical (i.e., non-text) form.

For example, it is well known in the art of neurological evaluation that eye movement and tracking is indicative of alertness and neurological well-being. The smartphone can be used as a tool to track eye movement and reaction time in response to certain stimuli. Typically, in the reverse camera mode shown in FIG. 4A, the enrollee's 401 image 124 of himself (and whatever background is present) fills the screen 425. With a custom app, the viewing screen presentation 425 can be divided showing a smaller image of the enrollee and his eyes (not shown), while another part of the screen can be used to show a variety of graphic images in various locations on the screen or moving across the screen (similar to screen presentation 225 in FIG. 2). The enrollee would have a contour on the screen to show the recommended distance of the phone from his face. Facial recognition can be used not only for ID, but also to make certain that the face is the proper orientation and distance from the reverse camera during the eye tracking evaluation.

The objects to be tracked can be as simple as a dot or a circle (see hexagon 210, FIG. 2). Images can also be flashed on the screen for various periods of time. Words and/or letters can be presented, and the enrollee can be asked to read the word or touch some image on the phone's LCD screen that relates to the word. This can be based on native language, but can also be language independent. Short term memory can also be tested by showing an image of an object, a letter, a number and asking the enrollee to indicate what he saw, and the sequence of what he saw by saying the name or number, or pressing a location on the LCD screen.

The most appropriate eye tracking system for evaluation, training or access will depend on the type of eye movements (i.e., fixations, saccades, and pursuits) that comprise the complex eye movements used for visual skills (e.g., spotting, localization, scanning, tracing, tracking) which are being evaluated/trained or tested for visually guided activities of daily living (e.g., reading, face recognition and television watching) or for access.

A history and data record of previous biometric sign-on and access control and test performance can be further used to build a profile that can be used to provide identification of the enrollee before, during and after the evaluation. A performance that is out of the curve for some reason can raise doubts on the authentication and identification process and result in a demand further access controls which may include third party verification (as in FIG. 3), or additional or repeated tests.

A simple test example is an application that shows a dot on the screen and instructs the enrollee to follow the dot's movement on the screen. This can be done by eye alone, or the enrollee could be asked to also follow with his finger. The size, shape and speed of dot can vary with the range of difficulty. Vibration can be tied to the testing such that the phone vibrates as long as the finger is on or near the moving dot, or vice versa. The movement of the dot is known, and the movement of the finger(s) can be registered from touch sensors on the screen. Alternatively, instructions can be given that if the phone vibrates, move the phone in some spatial pattern. This can also be used to test pain and range of motion in elderly patients, especially those who might have trouble coming in for examinations. The requested movement could be accompanied by verbal and visual and tactile clues. Vibration is an important clue in that it should be in contact with the enrollee and can enhance kinetic cues in addition to images and sounds.

Balance and direction can also be tested by moving the smartphone through space at the proper orientation based on graphic or verbal instructions sent to the enrollee. This can further evaluate the ability of the enrollee to perform certain tasks.

In all such tests, the tests and test scores can be remembered for comparison and also for assessment and allowing access to a vehicle or other access. Nuanced enrollee ID can be based on tilt, angle, key touch location and timing. This can be combined with running tests to enhance enrollee ID.

The profile of the enrollee can include personal ID and at least one other attribute such as age and gender. Other attributes can be added as desired. A profile can be constructed that creates a benchmark for certain activities and reaction times compared to people with the same or similar characteristics in the larger population.

Figure 4A:
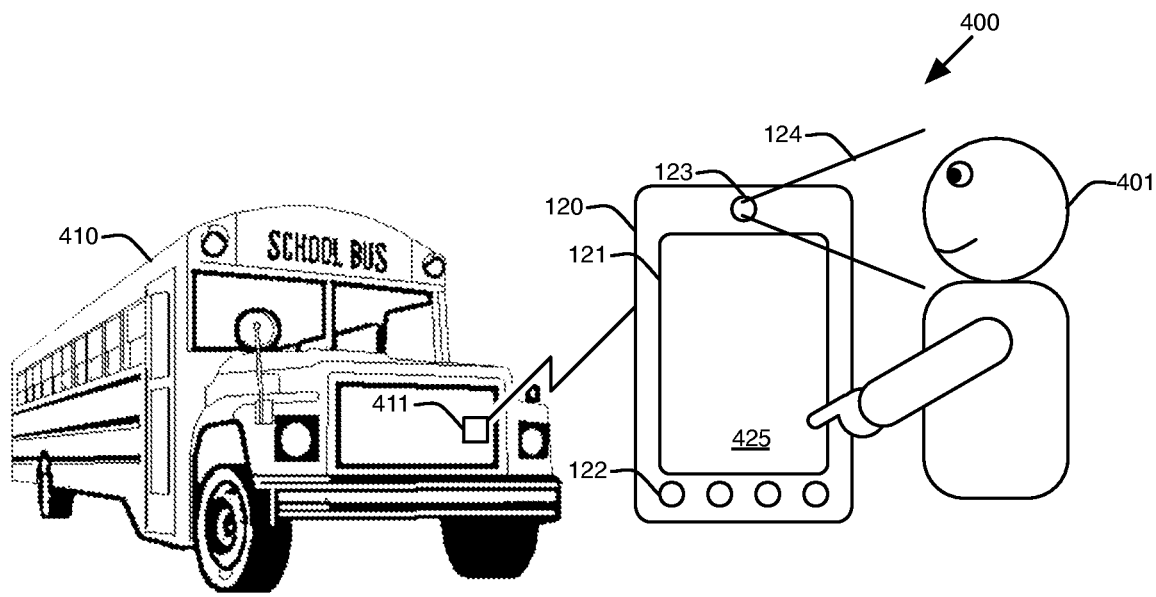
FIG. 4A shows a smartphone-based secure health testing and access system connected to the OBD connector of a vehicle for access control.
Figure 4B:
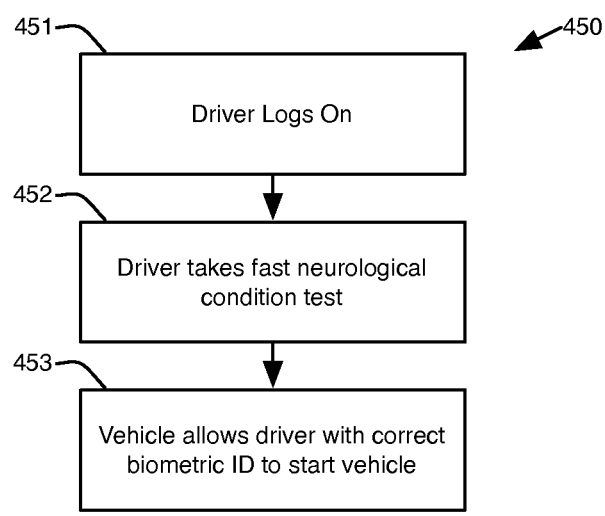
FIG. 4B is a flowchart for that secure access process.

FIG. 4A illustrates another embodiment of the invention, where the alertness testing application on the smartphone 120 can be tied by wire or wirelessly to a vehicle 410 or machine access control device. This may not be only for access, but also for authenticated transactions coming through the vehicle's dashboard application. This may also be tied to vehicle identification such as a license plate. Access to drive can also be tied to access to goods and services in a specific location based on the smartphone and its communication link with the vehicle, the identity of the vehicle and the identity of the driver as determined via the driver's smartphone, which can be running one of the applications previously described.

In a modern vehicle 410, a smartphone application can be tied to the OBD (on-board diagnostic) connector 411 standardized by the Society of Automobile Engineers (SAE), or other, which may be provided with a wired or wireless interface, that allows certain individuals to access a vehicle based on photos and perhaps a phrase and/or voiceprint sent from the smartphone to a remote control center and an access code sent to the phone via cellular modem, and then from the phone 120 to the vehicle 410 via OBD 411. This is very efficient in that the command itself can be matched with an authenticated voiceprint.

For example, in some instances access would be allowed based only on photo-based identification, while other access could be authenticated via face and voice, depending on policy. Such applications can also be tied to general access and the phone's GPS, user ID (UID, i.e., username) and password could be used in addition to facial and voice recognition. The back-facing camera image of the enrollee's face would have to be consistent with stored images and consistent during the testing and evaluation. A series of images, numbers, words can be shown to the enrollee. This could also be as simple as asking the enrollee to hold the main screen up to a mirror while he sees specific letters (mirror corrected in the application) and other images for his recognition and verbal confirmation. If not performed properly within a set period of time, the test is failed, and access to a vehicular asset (e.g., 410) could be denied. This is summarized by the testing and access process 450 shown in FIG. 4B, which begins at step 451 when the enrollee 401 (the driver) logs on to the smartphone 120 application. At step 452, the driver takes a brief test, e.g., to test his current neurological condition. Upon verifying the test was passed, at step 453, the smartphone 120 communicates via the OBD connection 411 and allow the driver, having demonstrated a valid identification and neurological state, to start the vehicle. The above test could also be used for medical and health assessment.

In some embodiments of the invention, enrollees are welcome to work together and share tests in health groups or independently. Health-based social networking is possible and encouraged. Activities and milestones such as pulse, blood oxygen, blood pressure, and alertness may all be used to form a general wellness status.

Figure 5:
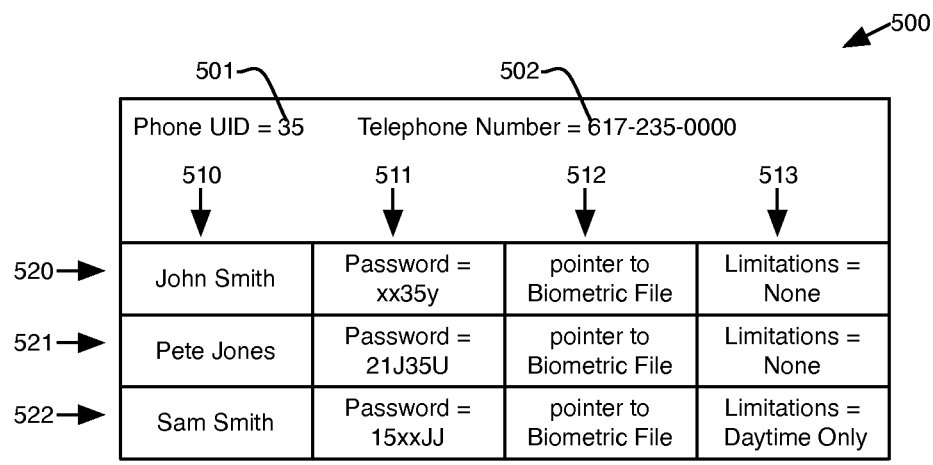
FIG. 5 shows a database record representative of multiple enrollees associated with a single mobile device.

In the preferred embodiment, one person is typically registered and tied to one mobile device; however, in other embodiments, such as shown in FIG. 5, multiple persons 510 can securely register and sign on (e.g., with the corresponding password 511 and biometric information 512, to a single, shared mobile device 501 and telephone number 502, or several devices (not shown), and the authenticated input from a plurality of secure devices can be collated and shared from a remote, secure database 112. Certain individuals 520, 521 may have no particular limitation 513, but other individuals (e.g., 522) may have access that is further limited (e.g., only allowed access during the daytime).

The present invention provides a unique way of using a smartphone to test, evaluate and control access that will prove cheap to implement and efficient to use.

Several descriptions and illustrations have been provided that aid in understanding the present invention. One with skill in the art will realize that numerous changes and variations can be made without departing from the spirit of the invention. Each of these changes and variations is within the scope of the present invention.

We claim:

1. An access control system comprising:
   a computer application adapted to be stored and executed on a processor in a mobile device having communication with a display screen, a first sensor, and a second sensor;
   said application configured to take a first biometric information of a participant with the first sensor, wherein said first biometric information is recorded in a data record;
   said application configured to make a measurement with a second sensor of a performance by the participant taking a test, the test comprising a presentation on the display screen, wherein the performance is representative of a neurological condition of the participant and the measurement is recorded in the data record;
   said application configured to control access by the participant to an asset based on at least said first biometric information and the measurement.

2. The access control system of claim 1 wherein the neurological condition is alertness, the presentation comprises images flashed on the display screen, the performance by the participant is to indicate what the participant saw, the second sensor comprises one of a touchscreen and a control, and the measurement comprises reaction time.

3. The access control system of claim 2 wherein the asset is a vehicle.

4. The access control system of claim 2 wherein the application has access to a second biometric information and access by the participant to the asset is allowed on the basis that the first biometric information is consistent with the second biometric information and the measurement indicates a valid neurological state, and access is denied otherwise.

5. The access control system of claim 1 wherein the asset is a vehicle.

6. The access control system of claim 5 wherein the mobile device communicates with the vehicle to control access through an on-board diagnostic (OBD) connection of the vehicle.

7. The access control system of claim 1 wherein said first biometric information comprises at least one of an image of a face, a voiceprint, a spoken pass-phrase and a fingerprint.

8. The access control system of claim 1 wherein the application has access to a second biometric information, and access by the participant to the asset is allowed on the basis that the first biometric information is consistent with the second biometric information and that the measurement indicates a valid neurological state.

9. The access control system of claim 1 wherein said measurement is of eye movement.

10. An access control system comprising:
    a computer application adapted to be stored and executed on a processor in a mobile device;
    said application configured to allow the participant access to an asset based on at least a first biometric information of the participant taken with a first sensor in communication with said mobile device
    and a neurological condition of the participant evaluated with a second sensor as a test is taken by the participant, the test presented on a display screen, the second sensor and display screen having communication with the mobile device.

11. The access control system of claim 10 wherein said neurological condition is further evaluated by measuring a reaction time to at least one operation requested in the test.

12. The access control system of claim 10 wherein said second sensor measures eye movement.

13. The access control system of claim 10 wherein the asset is a vehicle.

14. The access control system of claim 10 wherein said first biometric information comprises at least one of an image of a face, a voiceprint, a spoken pass-phrase and a fingerprint.

15. The access control system of claim 10 wherein said application has access to a second biometric information and access by the participant to the asset is allowed only when the first biometric information is consistent with the second biometric information.

16. A method for access control comprising:
    providing a computer application adapted to be stored and executed on a processor in a mobile device, the mobile device having access to an account for a participant, the account comprising a first biometric information of the participant recorded in a database;
    accepting with the application a second biometric information taken with a first sensor of the mobile device;
    presenting a test to be taken by the participant with the application on a display screen of the mobile device;
    making a measurement with the application of a performance by the participant during the test, the measurement made with a second sensor of the mobile device, the measurement indicative of a neurological condition of the participant; and,
    one of allowing and denying the participant access to an asset based on a match of said first biometric information and the second biometric information and further based on the measurement.

17. The method of claim 16 wherein the asset is a vehicle.

18. The method of claim 16 wherein said measurement comprises a reaction time to at least one operation requested in the test.

19. The method of claim 16 wherein said second sensor measures eye movement.

20. The method of claim 16 further comprising:
    recording the measurement in the database with the application, such that the measurement is tied to the account;
    sharing access to the account with others.

* * * * *